US006608670B2

United States Patent
Nottke et al.

(10) Patent No.: US 6,608,670 B2
(45) Date of Patent: *Aug. 19, 2003

(54) LASER VERIFICATION AND AUTHENTICATION RAMAN SPECTROMETER (LVARS) DETECTING THE STOKES AND/OR ANTI-STOKES EMISSION

(75) Inventors: Francis A. Nottke, Tucson, AZ (US); James A. Kirchoff, Phoenix, AZ (US); Jonathan N. Lucke, Tucson, AZ (US); John Pollard, Tucson, AZ (US)

(73) Assignee: Wizard of Ink & Co., Tucson, AZ (US)

(*) Notice: Subject to any disclaimer, the term of this patent is extended or adjusted under 35 U.S.C. 154(b) by 48 days.

This patent is subject to a terminal disclaimer.

(21) Appl. No.: 09/908,453

(22) Filed: Jul. 18, 2001

(65) Prior Publication Data

US 2002/0048013 A1 Apr. 25, 2002

Related U.S. Application Data

(63) Continuation-in-part of application No. 09/450,897, filed on Nov. 29, 1999, now Pat. No. 6,275,285, which is a continuation-in-part of application No. 09/270,415, filed on Mar. 16, 1999, now Pat. No. 6,008,888.

(51) Int. Cl.[7] .............................. G01J 3/44; G01N 21/65
(52) U.S. Cl. ..................... 356/71; 356/301; 356/307
(58) Field of Search ......................... 356/301, 71

(56) References Cited

U.S. PATENT DOCUMENTS

| | | | |
|---|---|---|---|
| 4,077,719 A | | 3/1978 | Barrett et al. |
| 4,405,237 A | | 9/1983 | Manuccia et al. |
| 4,512,660 A | | 4/1985 | Goldberg |
| 4,529,305 A | | 7/1985 | Welford et al. |
| 4,799,786 A | | 1/1989 | Gerrard |
| 5,206,699 A | | 4/1993 | Stewart et al. |
| 5,801,819 A | | 9/1998 | Spear et al. |
| 6,091,491 A | * | 7/2000 | Chisholm et al. ........... 356/301 |
| 6,108,081 A | | 8/2000 | Holtom et al. |
| 6,275,285 B1 | * | 8/2001 | Nottke et al. .................. 356/71 |

FOREIGN PATENT DOCUMENTS

WO    WO 91/11703    * 8/1991  .................. 356/301

* cited by examiner

*Primary Examiner*—F. L. Evans
(74) *Attorney, Agent, or Firm*—Jon A. Gibbons; Fleit,Kain,Gibbons,Gutman & Bongini P.L.

(57) ABSTRACT

The LVARS is a fully instrumental, non-destructive spectroscopic device for the analysis and verification and authentication of the optical and electromagnetic properties (OEMP) of the inks, dyes, thin films, plastics, toners, paper, fixatives, paints, and printing agents used in documents and financial instruments. The instrument is quantitative in nature so as to correlate compositional data (elemental, isotopic, structure) with Raman optical spectra. The LVARS design consists of a computer-controlled spectrometer with a microscope-guided grid head containing the laser excitation source and detector and optics.

29 Claims, 7 Drawing Sheets

LASER VERIFICATION AND AUTHENTICATION RAMAN SPECTROMETER (LVARS) DETECTING THE STOKES AND/OR ANTI-STOKES EMISSION

CROSS-REFERENCE TO RELATED APPLICATIONS

This is a continuation-in-part of patent application Ser. No. 09/450,897 filed on Nov. 29, 1999, now U.S. Pat. No. 6,275,285 B1, which is a continuation in part of patent application Ser. No. 09/270,415 filed on Mar. 16, 1999, now U.S. Pat. No. 6,008,888 issued on Dec. 28, 1999, which is commonly assigned herewith to The Wizard of Ink & Co., and each of the above referenced patents are hereby incorporated hereinto in there entirety by reference.

BACKGROUND OF THE INVENTION

1. Field of the Invention

The invention disclosed broadly relates to the field of spectroscopic analysis, and more particularly relates to the field of Raman spectroscopic analysis (both qualitative and quantitative) for the authentication of the optical and electromagnetic properties of inks, dyes, thin films, plastics, toners, paper, fixatives, paints, printing agents and other written materials. The invention disclosed also broadly relates to the field of Raman spectroscopic analysis for the authentication of the optical and electromagnetic properties of organic and inorganic compounds, for both natural as well as manufactured materials.

2. Description of the Related Art

The investigation of authenticity, and in particular, the discovery of a forgery, are problems that have plagued man since antiquity. One early target of forgery was currency and many laws were passed to thwart counterfeiting. Today, fraudulent activity encompasses much more than paper currency. It can include business and legal documents, credit cards, checks, other financial media, art, antiquity materials, and documented security threats to person(s) and/or institutions.

The loss of valuable resources, man-hours, and associated assets due to fraudulent documents and financial media are escalating daily in the United States and other parts of the world. Part of the problem is that there are no predominantly established, widely accepted protocols between government agencies, business, and academia to prove authenticity. The primary difficulty stems from a lack of an instrumental solution. Currently there is no automated mechanism or method to analyze documents or financial media which takes into account accurate age dating, the precise matching of varying ink samples, and alteration of a genuine article. Every year, hundreds of thousands of working hours are devoted to analyzing documents and financial media in order to curb the billions of dollars of losses in the domestic and international markets. The incurred monetary loss is mainly due to check, credit card, and paper currency fraud.

Unfortunately, technology which is available to the average consumer continues to remain on par with the processes used to create original financial media and assorted legal documentation by both government and corporations. Color copiers, scanners, multimedia software, laser printers, and desktop publishing software are among the tools which modern day criminals can use to create a forgery. Local, state, and federal law enforcement agencies as well as financial institutions are calling for an automated mechanism or method by which the expedient authentication of legal and financial documents, and documents threatening persons or institutional security can be established. Accordingly, a need exists to provide a method and system to aid in the verification of documents and other media.

Historically, a variety of techniques have been used for the analysis of inks, dyes, thin films, plastics, and written materials. One easy technique to thwart counterfeiting was the use of multicolor printing. This technique, although useful, is not without its shortcomings. The wide availability of color printers and especially full color copiers has greatly reduced the effectiveness of multicolor printing to stem counterfeiting.

Other techniques for the analysis of inks, dyes, thin films, plastics, and written materials are adaptations of classical wet chemistry analysis where a document or ink sample is subjected to a variety of solvents and chemically reactive agents. These chemical reactions are then compared to a known sample using the human eye and microscopic examination. Other forms of wet chemistry analyses involve spot tests on inks and documents which incorporate a light source to excite various chemicals. While useful, these classical wet chemistry analyses suffer from several shortcomings.

First, these classical wet chemistry analyses have proven to be highly unreliable as they involve personal, subjective judgments, even the opinions of experts may vary from one to another. Second, these techniques cannot accurately distinguish between different samples of ink. Third, the use of wet chemistry techniques cannot age-date within a single sample of ink. Fourth, these techniques do not provide a method to determine the origin of the document. Fifth, the use of these wet chemistry techniques is destructive and therefore makes the analysis difficult to repeat when necessary. Destructive techniques are highly undesirable, especially for application on rare or historic documents, and on evidence used in trials. Sixth, the use of classic wet chemistry is cumbersome because it requires hand-to-sample manipulation. A wide range of chemical tests have been developed during this century, but none have proven accurate over a range of samples. Most of these tests are micro-scale. This makes them difficult to perform, difficult to repeat, destructive in almost all cases, and subject to wide variety of environmental contamination. Seventh, few forensic methods have been developed to calibrate these tests. For example, thin-layer chromatography (TLC) has been used to analyze very small flakes of ink and dyes, but this technique, at best, is merely qualitative, not quantitative. Eighth, and perhaps most important, forgers have developed techniques to overcome wet chemistry analysis.

Inks, dyes, thin films, plastics, and written materials can be analyzed using automated comparison which incorporates spectral analysis using light sources of different wavelengths. However, this suffers from several major problems: wavelengths are polychromatic, energy is either too high or too low and the final examination has to be done by eyesight once again. Even when the best light sources are used, such as lasers, in conjunction with the best detectors, the results are still qualitative, not quantitative, due to damage to the sample from analysis, or the lack of any standards for comparison. Moreover, the current spectral analysis of credit cards suffers from several weaknesses. There is the destruction of the sample as well as the inability to differentiate between a genuine card and a genuine card that has been altered (as opposed to a total forgery). Document analysis has attempted to develop techniques for age dating using basic chemistry, but this is simply not sophisticated enough.

One technique for the analysis of inks, dyes, thin films, plastics, and written materials is scanning electron microscopy-electron diffraction x-rays (SEM-EDX). The technique of SEM-EDX overcomes some of the problems with earlier techniques, but still suffers from shortcomings. First, SEM-EDX is not accurate due to a wide variety of environmental contamination such as particulate matter. This contamination interferes with the accurate microscopic compositional sample determination. Second, with SEM-EDX, there is almost no spatial accuracy for differing elemental concentrations at the sub-micron level. Third, although SEM-EDX is used to determine specific elements present qualitatively, the SEM-EDX technique cannot distinguish on a small scale the precise location of a quantitative amount. Fourth, SEM-EDX cannot determine organic species, which comprises the majority of the samples used in document authentication and financial instruments.

Another technique for the analysis of inks, dyes, thin films, plastics, and written materials is magnetic ink character recognition (MICR) analysis. However, MICR cannot be used for the analysis of financial media and many identification systems because such documentation uses strips of magnetic material for information storage. An analysis conducted using MICR would destroy stored material within the magnetic strip, and in turn, the magnetic material would provide questionable results.

Recently, a new technique incorporating Raman spectroscopy has been used for the analysis of artwork, ancient documentation, as well as more recently printed material. The Raman analysis of art has not yet proven itself quantitative nor has it been optimized for non-metallic species (organic). In addition, current Raman technology developed specifically for the analysis of inks and dyes (FNF Foram 6500) is also incapable of quantitative analysis, possibly destructive, and subject to fluorescence and back-scattering interference.

The main problems that all previously mentioned techniques suffer from are an inability to yield quantitative measurements in either elemental or molecular analysis, a destruction of evidence, the inability to determine that degree of destructiveness, and the inability to distinguish between molecular or oxidation states which makes age verification and artificial aging detection by photolysis or heat impossible. These techniques are inaccurate because their produced results are not quantifiable. They are cumbersome in that they require hand-to-sample manipulation on written words and because they lack spectroscopic inter-comparison. Hence, the need exists for an apparatus to perform a quantitative, non-destructive, accurate, precise (reproducible across a range of samples), elemental and molecular specific, analysis of inks, dyes, thin films, plastics, toners, papers, fixatives, paints, printing agents, and other written materials.

SUMMARY OF THE INVENTION

The LVARS system is a fully instrumental, non-destructive spectroscopic device for the analysis and verification and authentication of the optical and electromagnetic properties (OEMP) of inks, dyes, thin films, plastics, toners, paper, fixatives, paints, and printing agents used in documents, financial instruments, art, and more. The LVARS system is quantitative in nature so as to correlate compositional data (elemental, isotopic, structure) with Raman optical spectra. The LVARS system consists of a computer-controlled spectrometer with a microscope-guided grid head containing the laser excitation source and detector and optics. The spectrometer contains signal processing electronics which sends a stream of data to the computer for analysis and correlation with the library database.

In another embodiment, the LVARS system is also capable of performing analysis and verification and authentication of the OEMP of organic and inorganic compounds, for both natural as well as manufactured compounds.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention will be apparent from the following detailed description taken in conjunction with the accompanying drawings.

DETAILED DESCRIPTION OF AN EMBODIMENT

However, it should be understood that these embodiments are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in the plural and visa versa with no loss of generality.

Figure 1:
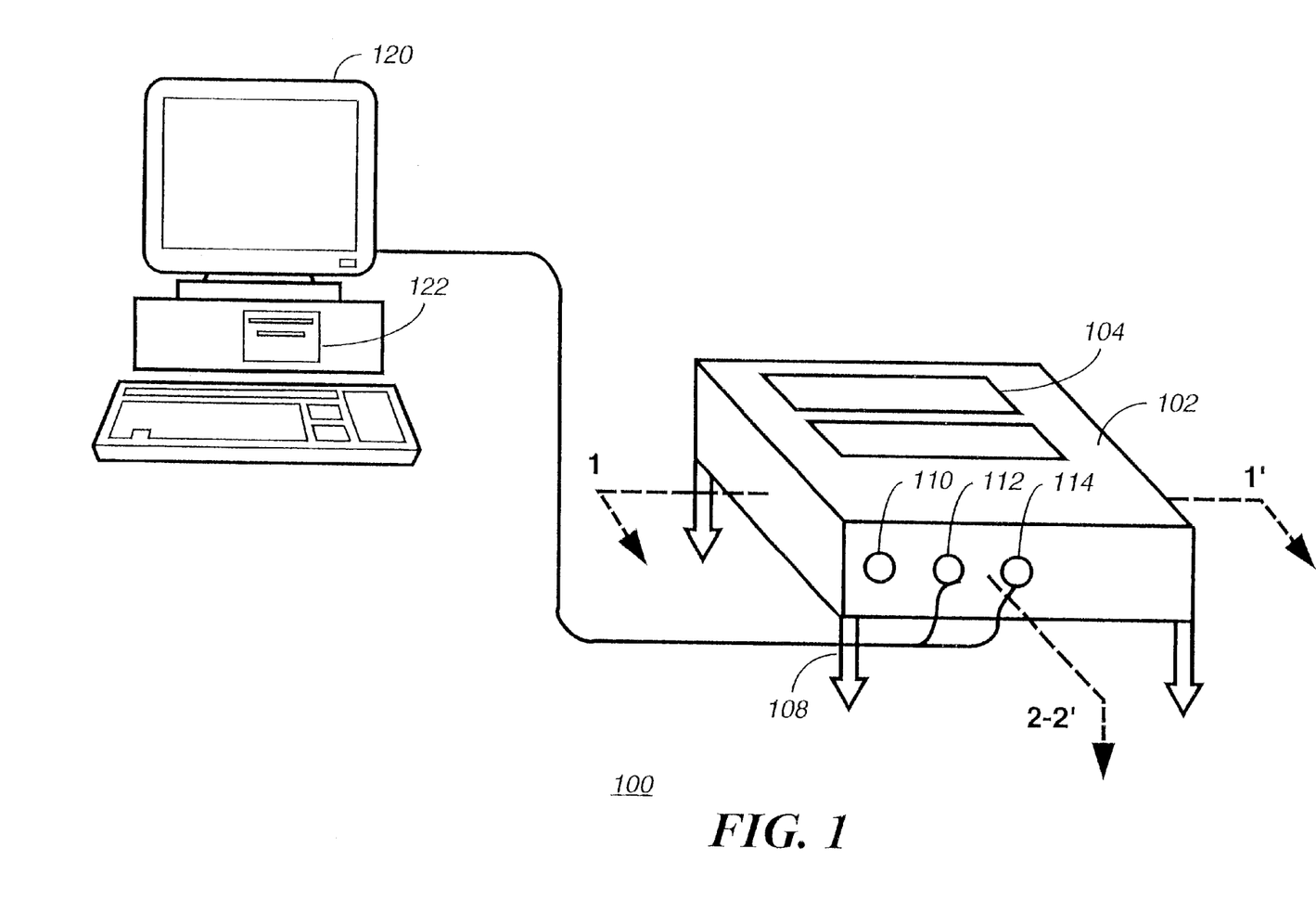
FIG. 1 is an elevational view of the LVARS system according to the present invention.
Figure 2:
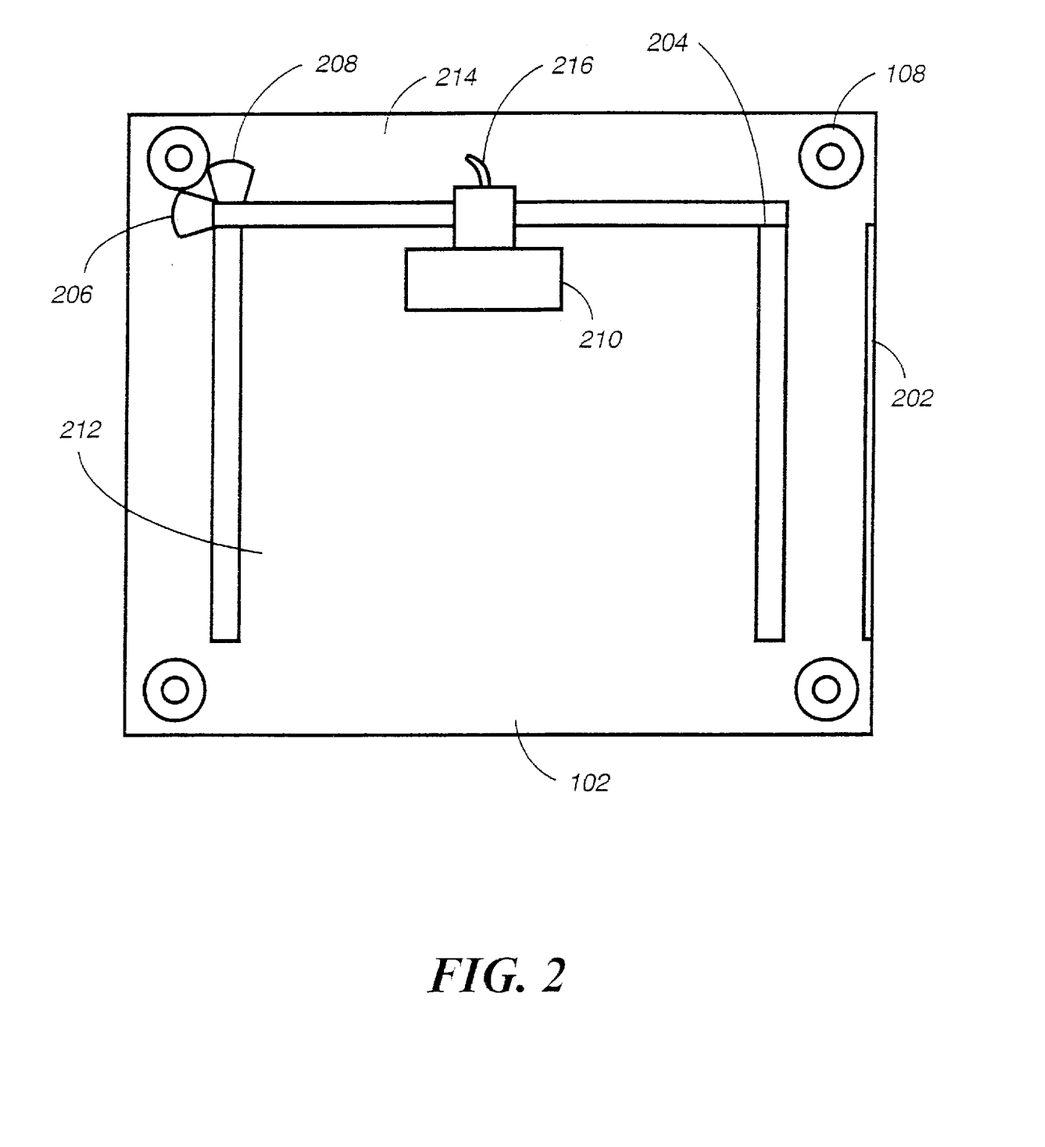
FIG. 2 is a cross-sectional bottom view of the examination module of FIG. 1 taken along axis X–X=showing the movable grid head assembly according to the present invention.

Turning to the figures, where like references refer to throughout several drawings, shown in FIG. 1 is an elevational view of an LVARS (Laser Verification and Authentication Raman Spectrometer) system 100 according to the present invention. The LVARS system 100 consists of a spectrometer apparatus 102 connected to a computer controller 120. The computer controller 120 is a general-purpose computer such as a laptop with standard interfaces such as a parallel port, serial communications, and network communications. In the computer controller 120, all processing and control programming is contained as well as a library database 122. The spectrometer apparatus 102 is designed to be portable. In one embodiment, the spectrometer apparatus 102 is approximately 30" in length by 30" in width by 25" in height, so that it can easily be transported from one location to another. Two access ports 104 are shown for accessing the internal components that will be discussed in FIG. 4 below. The spectrometer is constructed with any nonmagnetic material that is chemically non-reactive and can be coated with a black powder coat finish so as to be non-spectroscopically active. One example of a nonmagnetic, chemically inert and non-spectroscopically active material is black anodized aluminum. The entire spectrometer apparatus 102 is supported by antivibration legs 108 such as pneumatic legs or similar supports. A variety of ports are coupled to the spectrometer apparatus 102 for interfacing to devices, such as a power port 110 for interfacing to an external power source; a data port 112 and a controller port 114 for communicating with computer controller 120. Although the computer controller 120 is a general-purpose computer, it will be understood to those skilled in the art, that any processor-based system can be used. Moreover, it is important to note, that these dimensions are exemplary only, and it will be understood to those skilled in the art, that changes can be made to the dimensions of the device without departing from the true scope and spirit of the invention FIG. 2 is a cross-sectional bottom view of the spectrometer apparatus 102 of FIG. 1 taken along axis X–X=showing the movable grid head assembly 210 according to the present invention. The entire spectrometer apparatus 102 forms a substantially rectangular chamber 212 in which a sample can be introduced into the chamber 212 through access door 202. An x-y table 204 with nanometer resolution, such as those available from Anorad Corporation or Burleigh Instrument Corporation is attached to the top inner side 214 of the spectrometer apparatus 102. In this embodiment, the linear area for both the x and y axis travel is about 0.6 meters, but other dimensions made be used. The movable grid assembly 210 is fastened to x-y table 204 so that it may be positioned by the x-y table 204. A cable feed 216 for carrying data communications, control and power connects the spectrometer apparatus 102 to the movable grid head assembly 210 and the x-y table 204.

Figure 3:
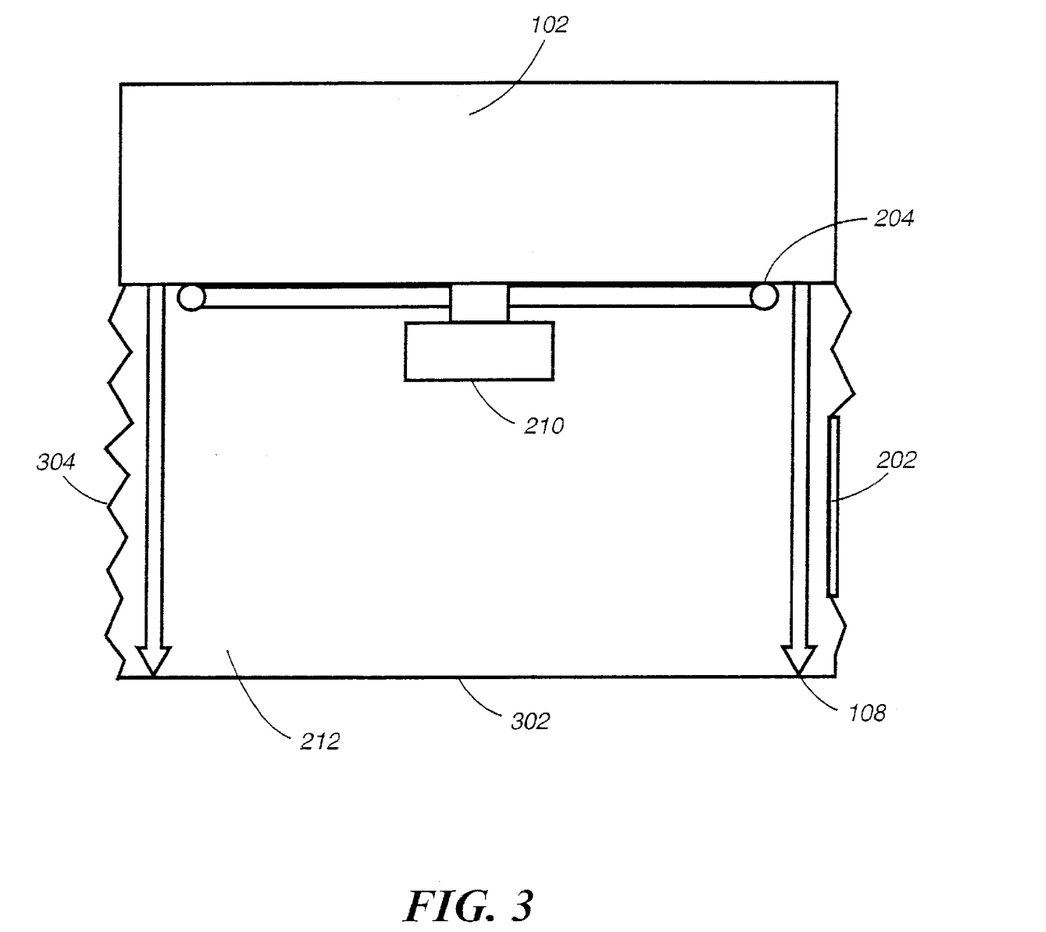
FIG. 3 is a cross sectional side view of the movable grid head of FIG. 1 taken along the axis Y–Y=according to the present invention.

Referring to FIG. 3, shown a cross sectional side view of the movable grid head assembly 210 of FIG. 1 taken along the axis Y–Y=according to the present invention. The spectrometer apparatus 102 supported by legs 108 with expandable side walls 304 for accommodating samples up to approximately 12" in height. The side walls, 304, the top under side 214 of the spectrometer apparatus 102 and a sample platen 302 form the substantially rectangular chamber area 212 which is isolated from ambient light to enable analysis of a specimen placed inside the cavity 212 via the access door 202. It should be understood to those skilled in the art that many mechanical configurations of the spectrometer apparatus 102 are possible to define a chamber 212 comprising of a variety of different geometric dimensions and shapes for analysis of samples is within the true scope and spirit of the present invention.

Figure 4:
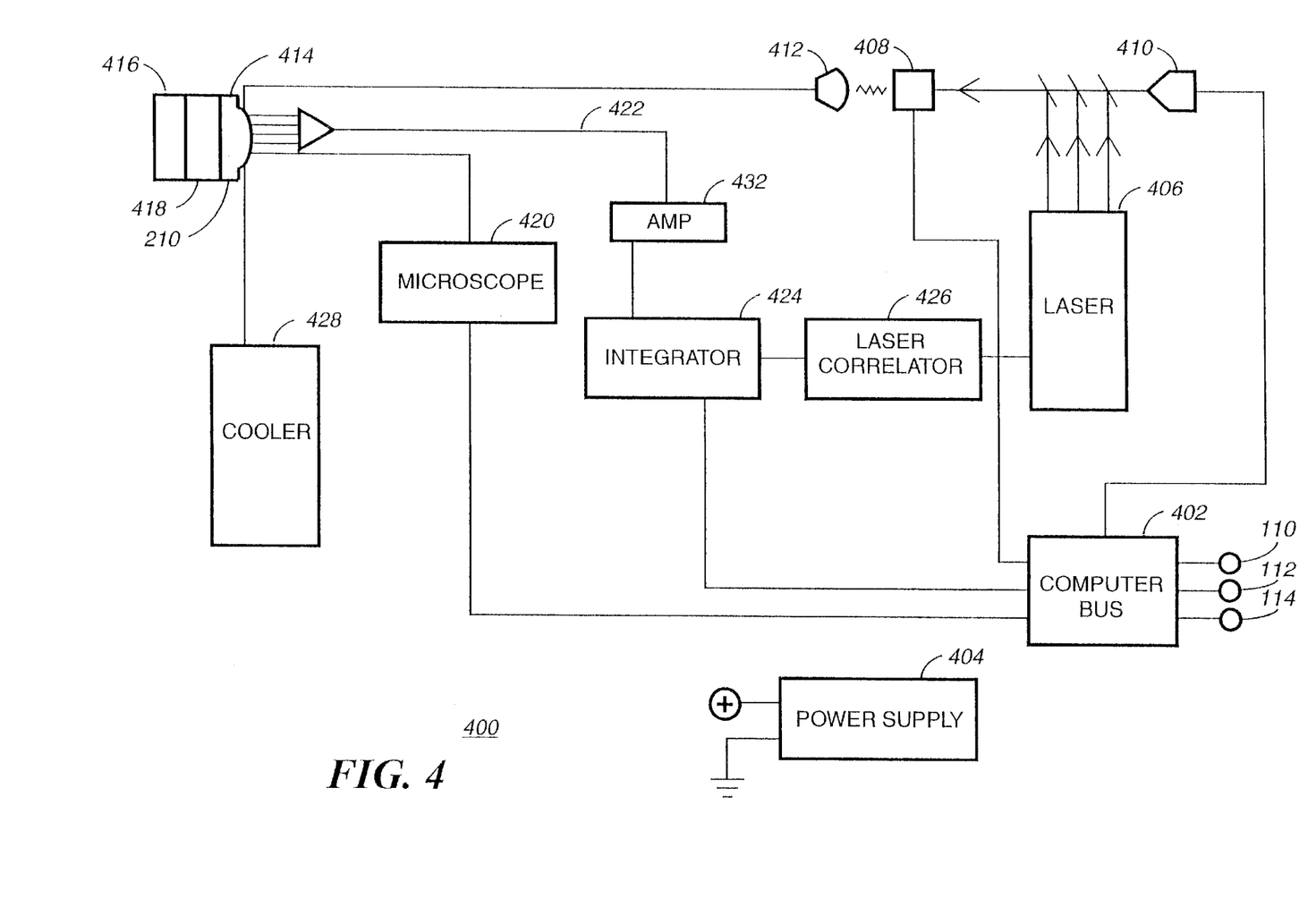
FIG. 4 is a block diagram of the major components of the spectrometer apparatus FIG. 1 according to the present invention.

The spectrometer apparatus 102 is described in further detail. Referring to FIG. 4 there is shown a block diagram 400 of the major components of the spectrometer apparatus 102 of FIG. 1 according to the present invention. A computer bus 402 such as a standard IBM Personal Computer Bus, a VME Bus, IEEE 488 Bus or equivalent acts as the controller backbone for the components in the LVARS system 100. As described in FIG. 1 above, a variety of ports 110, 112 and 114 interface to the computer bus 402 for communicating with computer controller 120. A stabilized power unit with feedback control 404 powers the components in the LVARS system 100. One typical stabilized power unit with feedback control 404 is available from LeCroy or EG&G. A multiple wavelength laser head supply 406 with diode lasers and (a) tunable laser(s) such as those supplied by Coherent or Spectra Physics, provides tunable multiple wavelength output. The laser head supply produces different wavelengths via solid-state diodes, which are chosen for their small size, low power requirement, low power output, and ease of maintenance, and (a) tunable laser(s), for scanning capability. The main strengths of Raman spectroscopy in the LVARS system 100 are the excellent specificity (both elemental or in-situ molecular), excellent spatial resolution, excellent sensitivity, and strong immunity to interference especially fluorescence. In this embodiment, the laser head supply 406 provides a range of the wavelengths from 200 nanometers up to 2000 nanometers. A computer controlled 360-degree translation stage mounted beam splitter and mirror 408 is coupled to laser head supply 406. The beam splitter and mirror 408 split the laser output from laser head supply between a laser beam power meter 410 and a laser light output-to-fiber coupler 412. One example of the laser beam power meter 410 is available from Burleigh or Coherent. The laser beam power meter 410 enables the laser output, including the laser power, laser beam profile and laser waveform from laser head supply 406 to be monitored via computer bus 402. The laser light output-to-fiber coupler 412 provides laser output to movable grid assembly 210. A cable feed 414 holds a combination of several types of cables (fiber optic data lines, control lines, power lines, and cooler lines) for movable grid assembly 210. First, fiber optic data lines include: the laser light output-to-fiber coupler 412 from laser head supply 406 and microscope view 416 coupled to a Zeiss brand microscope 420 or equivalent. Second, control lines include: microscopic control cables 418 from microscope 420 for controlling the focus of the microscope view and detector data lines 422 from the multiple detectors in the movable grid head assembly which will be discussed in further detail below. The detector data lines 422 are connected to the boxcar integrator 424 for combining the data on detector data lines 422. It is important to point out the multiple data paths to integrator 424. The integrator 424 is a boxcar type integrator such as those available from Stanford Research Systems or equivalent. The integrator 424 is coupled to a laser correlator 426 for providing a correlative feedback to laser supply 406. This enables the laser supply 406 to be adjusted to give a desired output as read by the detectors for a given laser wavelength, power and beam profile. A thermoelectric cooler 428 is coupled to the detectors in the movable grid head assembly 210 for maintaining the detectors in a predetermined operating temperature range. In this embodiment, the predetermined operating range is between –200 and +40 degrees centigrade and an Oxford Systems brand thermoelectric cryostat or equivalent is used.

It is important to note that this embodiment is exemplary only and that many changes are possible to the above configuration without departing from the true scope and spirit of the invention. In particular, adaptations to the above include (i) changes in the standard size of the chamber 212 to accommodate different samples; (ii) other hardware and software can be substituted in place of the computer bus 402, as the controller backbone for the components in the LVARS system 100; (iii) any number of ports 110, 112, 114 can be used depending on the configuration of the LVARS system 100; (iv) laser 402 with better or equivalent capabilities; and the functions of the boxcar integrator 424 can be implemented in many combinations of hardware and software.

Figure 5:
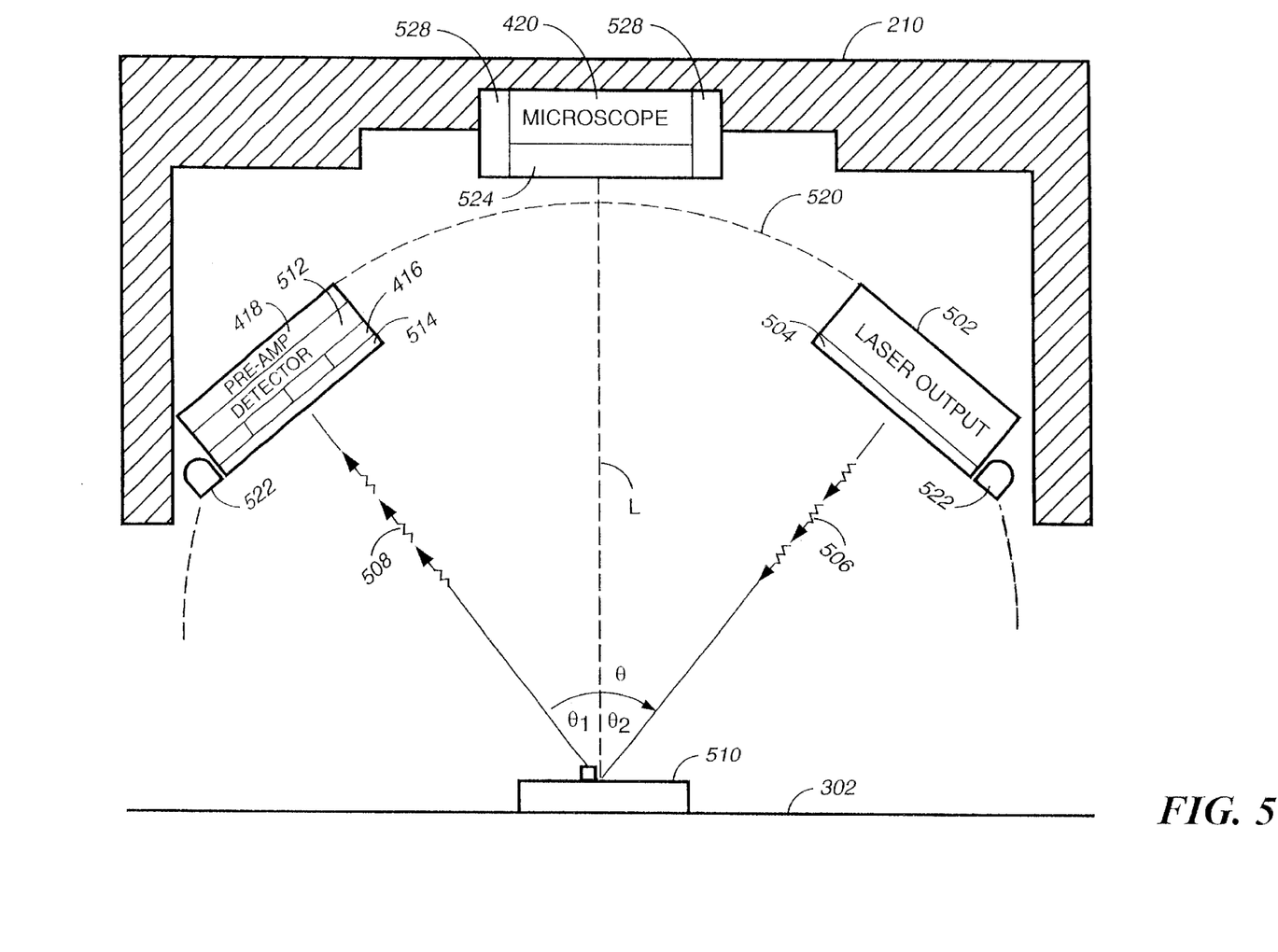
FIG. 5 is a block diagram of the movable grid head of FIG. 2 according to the present invention.

FIG. 5 is a block diagram 500 of the major components of the movable grid head assembly 210 of FIG. 2 according to the present invention. A laser output head assembly 502 and a detector head assembly 512 are slidably mounted on an arc-shaped track 520. A pair of servo controlled motors 522 enables the output head assembly 502 and the detector head assembly 506 to be individually positioned anywhere along the arc-shaped track 520. This ability to independently position both the output head assembly 502 and the detector head assembly 512 provides a range of adjustment between 0° and 180° for the angle of analysis S. As shown in FIG. 5, the angle of analysis S is defined by the angle of incidence $S_1$ plus the angle of reflection $S_2$. Stated mathematically, the angle of analysis is $S=S_1+S_2$ where line L is perpendicular to sample 510 resting on sample platen 302 of spectrometer apparatus 102. Accordingly, the angle of analysis S corresponds to the output 504 of output head assembly 502 and the laser emissions 506 to sample 510, and the Raman spectra 508 from 510 and can be adjusted such that 0° #S #180°. The mounting method shown in FIG. 5 is exemplary only and other configurations are possible to provide an adjustable angle of incidence S.

The output head area 502 is coupled to the laser light output-to-fiber coupler 412 from the Raman laser head supply 406. The output 504 of laser head assembly 502 is focused on sample 510 using a computer-controlled lens 504. The Raman spectra 508 are directed by holographic grating 514 and are detected by detectors 416. The holographic grating 514 filters scattered light and any other device which can separate light based on its wavelength and energy, may be used in place of a holographic grating without departing from the spirit and scope of the present invention. The detectors 416 are comprised of multiple detectors. These detectors 416 include: a real-time-full frame charge couple detector (CCD) which is available from EG&G; a photo-multiplier such as those available from Hamamatsu; an infrared InGaAs or similar; and a Ge(HPGe/Si(Li)) detector or similar from Oxford Systems. A computer controller preamp 418, such as Hamamatsu, is connected to the connector heads 416 prior to being fed to integrator 424. The integrator 424 rejects scattering and fluorescence signals that mask the Raman spectra. In addition, the integrator 424 is coupled to the laser supply 406 through laser correlator 426 to enable both spatial and temporal resolution to be correlated. A computer-controlled aperture 524 is connected to visible light microscope 420. A set of computer controlled white lights 528 or light ring with adjustable light intensity is included for manual observation with the eye to ensure accurate laser head assembly 502 and detector head 512 alignment. The use of a very accurate x-y positioner, combined with a very accurate laser head assembly 502 and detector head 512 alignment enables accurate spot placement and analysis sizes on the order of 0.10 to 1.0 micrometers. In an alternate embodiment, a CCD camera is coupled to the microscope to enable the display of the sample 510 being analyzed on a monitor (not shown). The detector head 512 of the LVARS system 100 combined with the very accurate positioning delivers a high resolution Raman signal. The spectral range of the detectors 416 in the detector head 512 are 200 to 8,000 $cm^{-1}$ with a spectral resolution from 0.05 $cm^{-1}$ to 10.00 $cm^{-1}$. With multiple laser excitation sources from 200 to 2000 nm and multiple detectors internal to the instrument, the LVARS has great flexibility to analyze varying samples 510. It will be understood to those skilled in the art, the movable detector grid head 210 of the LVARS system 100 has complete spatial resolution control. In addition, computer controller 120 guides and monitors Raman excitation head 406, optics 504, microscope 420 and movable grid head assembly 210 functions in the spectrometer LVARS system 100.

Figure 6A:
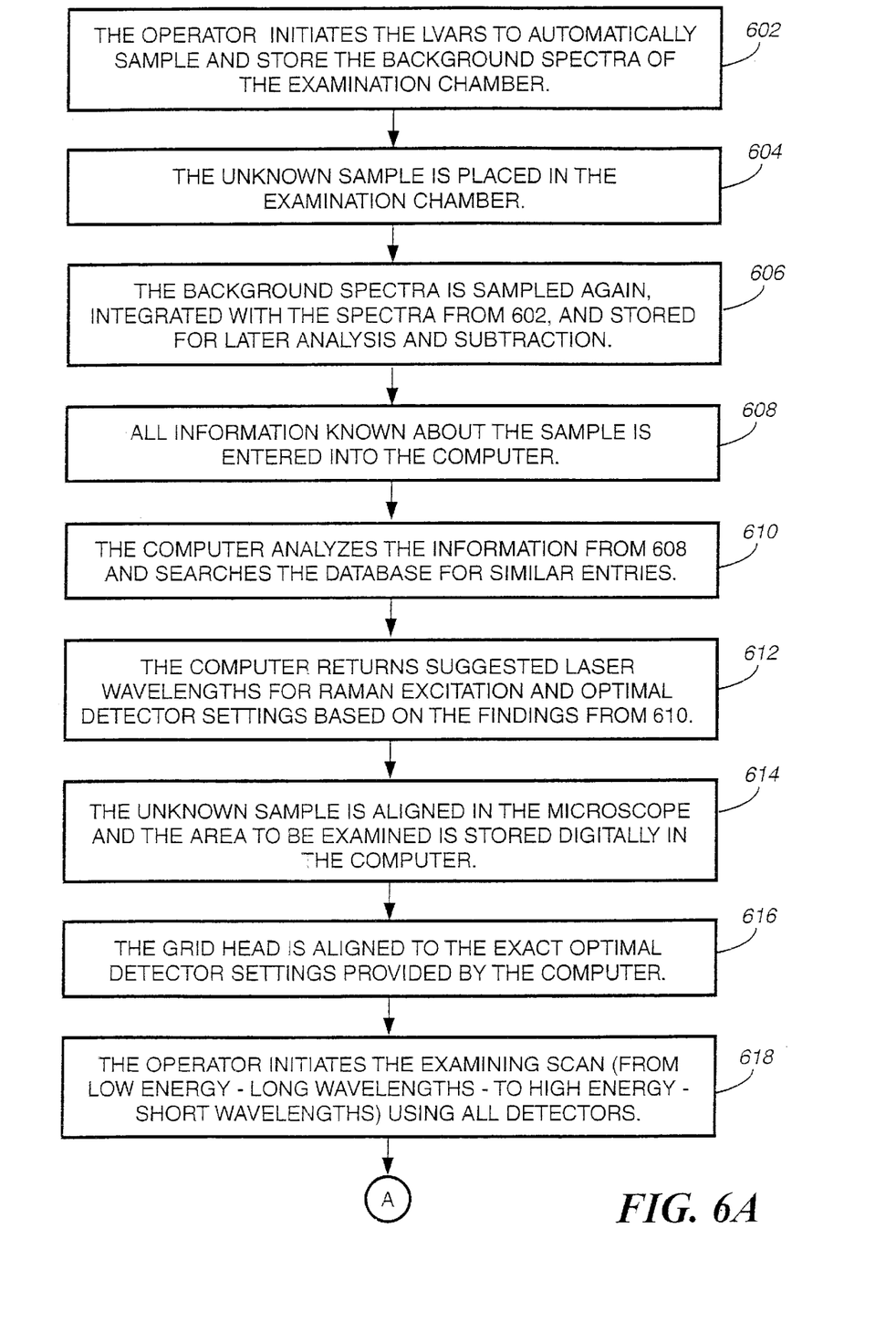
FIG. 6 is a flow diagram of the process performed by the LVARS system according to the present invention.
Figure 6B:
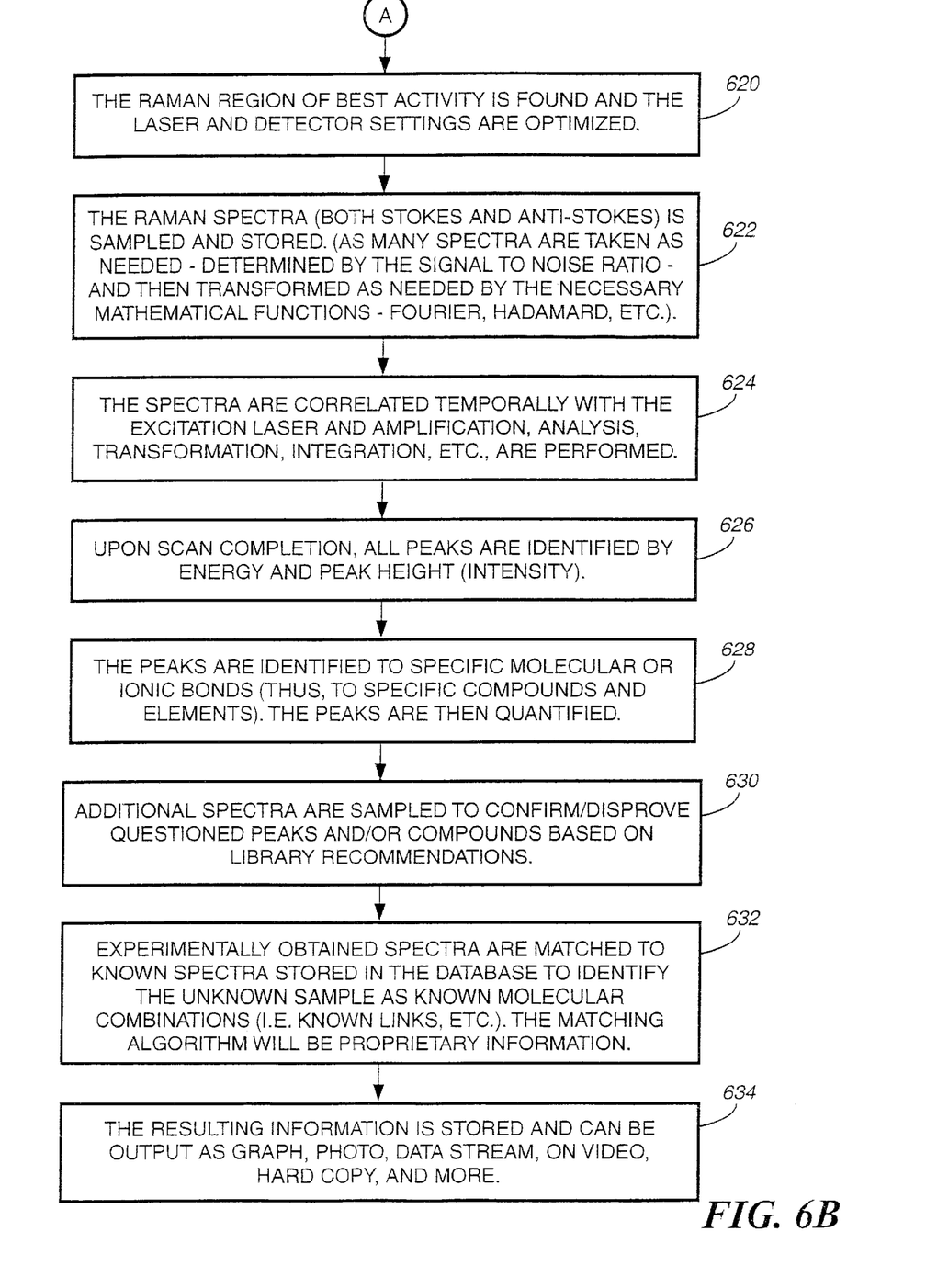

Referring now to FIG. 6 is shown a flow diagram of the process performed by the LVARS system 100. The process begins with reading the background spectra of the chamber without a laser and all the detection devices turned on, step 602. These detection devices include the microscope 420 with lights 528 shut off and detectors 416 in detector head assembly 512. This value should be negligible and the value is stored in the computer database 122 for subtraction later.

If there is background spectra measured over a certain threshold, a determination must be made if the background spectra is from the equipment of the LVARS system 100 itself such as a camera (not shown) or detector head assembly 512. Next, in step 604, an unknown sample 510 is placed into sample chamber 212 of the spectrometer apparatus 102. In step 606, the background spectrum is taken without turning on the laser output 506 in laser output head assembly 502 and turning on all the detection devices. Typically these background spectra should be negligible as measured with all detector devices. As before in step 602, if there is background spectra measured over a certain threshold for the type of sample entered in the database 122, a determination must be made if the background spectra is from the equipment of the LVARS system 100 itself such as a camera (not shown) or detector head assembly 512 or the sample 510 itself. There are methods known to determine the source of the background spectra. It should be noted that some samples give off phosphorescence that can interfere with the Raman signal 508 from the sample 510. The sample region may have to be selected if the sample gives off phosphorescence. The grid head assembly 210 may have to be positioned to a very small region using x-y positioning apparatus 204. For example, suppose the sample 510 is printed ink on paper and the paper phosphoresces. This is common with recycled paper. The area of analysis of the grid head assembly may have to be narrowed to one character or even portion of a character for the printed ink to avoid measurements masked by the paper on the sample 510. The background spectra of the sample may be mathematically integrated on computer 120 for analysis and subtraction later. Information on the background spectra of the sample is also used to scan the database 122 for similar known samples.

When the sample 510 is placed in the sample chamber, information is entered into the LVARS system 100 regarding the type of sample to be taken, for example, ink, paper, and any other sample properties known, step 608. In addition, in step 608, any physical and chemical properties are entered in computer 120. All these known quantities are stored in database 122 of computer system 120. At this point, the computer 120 begins scanning the database 122 for known samples with similar properties, step 610.

Next the laser irradiation of sample 510 begins, step 612. The strength of the irradiation signal 508 from sample 510 varies widely. If there are known samples matched in the database from the steps above, this information is used to set the laser 406 settings, step 614. If the sample 510 does not match any known samples stored in the database, then microscopic alignment on the sample is made for the target area, step 616, and a series of scans begins from low energy (long wavelength) to high energy (short wavelength) using the diode and tunable laser 406, while all the detectors 512 are turned on, step 618. When the Raman spectra region of highest activity is found, the detectors 512 and the associated preamp 418 and amplifier 432 settings are optimized, step 620. The optimization consists of adjusting the amplification for the detectors 512. The less amplification from the detectors 416 that is needed, the less possibility of injecting unwanted noise into the signal or degrading the signal-to-noise ratio from the detector. The Raman spectra is sampled, transformed, and stored, step 622, where the Raman spectra includes at least one Stokes or Anti-Stokes component or a combination thereof.

The boxcar integrator correlated to the wavelengths of laser 406, examines both the laser signal as well as the background spectra from step 612 and performs an integration, amplification, and conditioning, of the signal, steps 624. The functions in step 624, comprises and mathematical manipulations of the Stokes and/or Anti-Stokes components. The integration and amplification allows for a signal to be detected different from the laser so as to account for any harmonics that may be present from the detectors 416.

Steps 626 and 628 perform analysis on computer 120 using the database library 122. Additional spectra are sampled to confirm or disprove questioned peaks and/or compounds based on library recommendations, step 630. The computer analysis takes the known information input in during step 616 such as whether paper and ink are being analyzed or toner on paper is being examined. This greatly reduces the amount of data in database 122 that has to be reviewed. Other types of data can include the types of papers, inks, dyes, toners, thin films, plastics, fixatives, paints, and printing agents used in documents and financial instruments and other printed materials. It is important to note that the type of data includes organic and inorganic compounds, as well as materials occurring naturally or that are manufactured.

The analysis includes Raman optical spectra correlated to compositional data (elemental, isotopic, structure), step 632. The analysis includes comparing the sample and its known quantities against previously entered data of correlated spectra in the database 122, step 616. The library database 122 consists of the correlated Raman spectra of previously analyzed reference specimens: their Raman spectra, their magnetic susceptibility, absolute elemental and isotopic composition, NMR (Nuclear Magnetic Resonance), molecular structure data, and mass spectral molecular identity. If no Raman spectra are available for comparison, the signal can be stored in database 122 as a new entry along with the other known properties entered in step 608 above. Finally, the output can be directed to a variety of devices including the database 122, video display on the computer 120 or equivalent, step 634. The LVARS system 100 can nondestructively evaluate thermal and photolytic effects for age dating by examining electronic bonding states (oxidation) and molecular decomposition products. The LVARS avoids being cumbersome by instrumentally manipulating the sample. Finally, the LVARS can determine document origin by chemically matching the daughter products to the apparent source.

Although a specific embodiment of the invention has been disclosed, it will be understood by those having skill in the art that changes can be made to this specific embodiment without departing from the spirit and scope of the invention. The scope of the invention is not to be restricted, therefore, to the specific embodiment, and it is intended that the appended claims cover any and all such applications, modifications, and embodiments within the scope of the present invention.

What is claimed is:

1. A method to analyze media for composition and authentication of a source of unknown media comprising the steps of:

exposing a sample of unknown media simultaneously to multiple wavelengths from multiple laser sources;

reading a Raman spectra of the sample of the unknown media through a variety of detectors each with a specific wavelength detection region using Raman spectroscopy, wherein the Raman spectra comprises at least one Stokes component and/or at least one Anti-Stokes component; and manipulating mathematically at least one of the Stokes component and/or at least one of the Anti-Stokes component.

2. The method according to claim 1, wherein the step of reading a Raman spectra includes reading a Raman spectra comprising at least one Stokes component and at least one Anti-Stokes component.

3. The method according to claim 2, wherein the step of manipulating mathematically includes manipulating a combination of the Stokes component and the Anti-Stokes component.

4. The method according to claim 1, wherein the step of exposing a sample of unknown media includes exposing an unknown media which is organic.

5. The method according to claim 1, wherein the step of exposing a sample of unknown media includes exposing a sample of unknown media which is inorganic.

6. The method according to claim 1, wherein the step of exposing a sample of unknown media includes exposing a sample of unknown media which is naturally occurring.

7. The method according to claim 1, wherein the step of exposing a sample of unknown media includes exposing a sample of unknown media which is manufactured.

8. A method to verify the origin of an unknown sample of a document comprising the steps of:

exposing a sample of unknown media simultaneously to multiple wavelengths from laser sources in order to create Raman emissions from the sample;

detecting the Raman emissions from the sample using two or more detectors each with a specific wavelength detection region, wherein the Raman emissions comprises at least one Stokes component and/or at least one Anti-Stokes component; and comparing the detected Raman spectra with Raman spectra previously stored in a database.

9. The method according to claim 8, further comprising the step of:

manipulating mathematically at least one of the Stokes component or the Anti-Stokes component.

10. The method according to claim 8, wherein the step of detecting the Raman emissions includes detecting the Raman emissions comprising at least one Stokes component and at least one Anti-Stokes component.

11. The method according to claim 10, wherein the step of detecting the Raman emissions includes detecting the Raman emissions includes manipulating a combination of the Stokes component and the Anti-Stokes component.

12. The method according to claim 8, wherein the step of exposing the sample includes exposing a sample of an unknown media which is organic.

13. The method according to claim 8, wherein the step of exposing the sample includes exposing a sample of an unknown media which is inorganic.

14. The method according to claim 8, wherein the step of exposing the sample includes exposing a sample of an unknown media which is naturally occurring.

15. The method according to claim 8, wherein the step of exposing the sample includes exposing a sample of an unknown media which is manufactured.

16. A computer readable medium containing program instructions for verifying the origin of an unknown sample, said program instructions comprising instructions for:

exposing a sample of unknown media simultaneously to multiple wavelengths from multiple laser sources;

reading a Raman spectra of the sample of the unknown media through a variety of detectors each with a specific wavelength detection region using Raman spectroscopy, wherein the Raman spectra comprises at least one Stokes component and/or at least one Anti-Stokes component; and manipulating mathematically at least one of the Stokes component and/or at least one of the Anti-Stokes component.

17. The computer readable medium of claim 16, wherein the programming step of reading a Raman spectra includes reading a Raman spectra comprising at least one Stokes component and at least one Anti-Stokes component.

18. The computer readable medium of claim 17, wherein the programming step of manipulating mathematically includes manipulating a combination of the Stokes component and the Anti-Stokes component.

19. The computer readable medium of claim 16, wherein the programming step of exposing a sample of unknown media includes exposing an unknown media which is organic.

20. The computer readable medium of claim 16, wherein the programming step of exposing a sample of an unknown media includes exposing a sample of unknown media which is inorganic.

21. The computer readable medium of claim 16, wherein the programming step of exposing a sample of an unknown media includes exposing a sample of unknown media which is naturally occurring.

22. The computer readable medium of claim 16, wherein the programming step of exposing a sample of an unknown media includes exposing a sample of unknown media which is manufactured.

23. A system for verifying the origin of an unknown sample of a document comprising:

a chamber for exposing a sample to a multiple wavelength laser source in order to create Raman emissions from the sample;

two or more detectors each with a specific wavelength detection region for detecting the Raman spectra, wherein the Raman spectra comprises at least one Stokes component and/or at least one Anti-Stokes component; and a computer for manipulating mathematically at least one of the Stokes component and/or the Anti-Stokes component.

24. The system according to claim 23, wherein the two or more detectors detect Raman spectra comprising at least one Stokes component and at least one Anti-Stokes component.

25. The system according to claim 24, wherein an integrator manipulates a combination of the Stokes component and the Anti-Stokes component.

26. The system according to claim 23, wherein the sample of unknown media is organic.

27. The system according to claim 23, wherein the sample of unknown media is inorganic.

28. The system according to claim 23, wherein the sample of unknown media is naturally occurring.

29. The system according to claim 23, wherein the sample of unknown media is manufactured or processed.

* * * * *